(12) United States Patent
Byerly et al.

(10) Patent No.: US 10,722,658 B2
(45) Date of Patent: Jul. 28, 2020

(54) REUSABLE MEDICATION DELIVERY DEVICE WITH REMAINING MEDICATION DETERMINATION CAPABILITY

(71) Applicant: Eli Lilly and Company, Indianapolis, IN (US)

(72) Inventors: Roy H. Byerly, Indianapolis, IN (US); Russell W. Perkins, Carmel, IN (US); Giorgio M. Sardo, Milan (IT)

(73) Assignee: Eli Lilly and Company, Indianapolis, IN (US)

( * ) Notice: Subject to any disclaimer, the term of this patent is extended or adjusted under 35 U.S.C. 154(b) by 155 days.

(21) Appl. No.: 16/075,744

(22) PCT Filed: Feb. 21, 2017

(86) PCT No.: PCT/US2017/018632
§ 371 (c)(1),
(2) Date: Aug. 6, 2018

(87) PCT Pub. No.: WO2017/147039
PCT Pub. Date: Aug. 31, 2017

(65) Prior Publication Data
US 2019/0038843 A1 Feb. 7, 2019

Related U.S. Application Data

(60) Provisional application No. 62/300,199, filed on Feb. 26, 2016.

(51) Int. Cl.
*A61M 5/315* (2006.01)
*A61M 5/24* (2006.01)

(52) U.S. Cl.
CPC .......... *A61M 5/31568* (2013.01); *A61M 5/24* (2013.01); *A61M 5/31551* (2013.01); *A61M 5/31543* (2013.01)

(58) Field of Classification Search
CPC ........ A61M 5/178; A61M 5/31; A61M 5/315; A61M 5/31565; A61M 5/31566;
(Continued)

(56) References Cited

U.S. PATENT DOCUMENTS

2002/0133114 A1* 9/2002 Itoh ................... A61M 5/14566
604/67
2011/0190693 A1 8/2011 Takatsuka et al.
(Continued)

FOREIGN PATENT DOCUMENTS

CN 102307605 1/2012
EP 1240913 9/2002
(Continued)

OTHER PUBLICATIONS

Patent Cooperation Treaty International Search Report and the Written Opinion of the International Searching Authority pertaining to International Application No. PCT/2017/018632; dated Jul. 5, 2017.
(Continued)

*Primary Examiner* — Jason E Flick
(74) *Attorney, Agent, or Firm* — Arthur C. H. Shum

(57) ABSTRACT

A reusable medication delivery device that can determine medication remaining in a simple fashion. The device includes a first sensor (200) for sensing when a cartridge is mounted in the device, and at least one second sensor for sensing a retraction of a drive member (160) that engages a cartridge plunger (132). The device includes a controller that determines, based on inputs from the first sensor and the at least one second sensor, that a newly installed cartridge is to be considered full or not full of medication. The controller calculates, after a medication delivery and based on an input from a means for determining an amount of medication delivered by operation of a dose delivery mechanism, and if
(Continued)

the cartridge was considered full when newly installed, a quantity of medication remaining in the installed cartridge after the medication delivery.

23 Claims, 4 Drawing Sheets

(58) Field of Classification Search
CPC .......... A61M 5/31533; A61M 5/31535; A61M 5/31536; A61M 5/31545; A61M 5/31548; A61M 5/24; A61M 5/31543; A61M 5/31551; A61M 5/31568
USPC ........................................................ 604/187
See application file for complete search history.

(56) References Cited

U.S. PATENT DOCUMENTS

| | | |
|---|---|---|
| 2012/0238960 A1 | 9/2012 | Smith et al. |
| 2013/0072897 A1 | 3/2013 | Day et al. |
| 2013/0310756 A1 | 11/2013 | Whalley et al. |
| 2014/0074041 A1 | 3/2014 | Pedersen et al. |
| 2014/0243750 A1 | 8/2014 | Larsen et al. |
| 2015/0174330 A1 | 6/2015 | Nagel et al. |
| 2015/0306316 A1 | 10/2015 | Bruggemann et al. |
| 2015/0320934 A1 | 11/2015 | Draper et al. |
| 2016/0008552 A1 | 1/2016 | Madsen et al. |
| 2016/0296702 A1 | 10/2016 | Rasmussen et al. |
| 2017/0023204 A1 | 1/2017 | Takeuchi et al. |

FOREIGN PATENT DOCUMENTS

| | | | |
|---|---|---|---|
| EP | 2060284 | 5/2009 | |
| EP | 2060284 A1 * | 5/2009 | ........ A61M 5/31525 |
| EP | 2468340 | 6/2012 | |
| WO | 2011064299 | 6/2011 | |
| WO | 2012004298 | 1/2012 | |
| WO | 2015123688 | 8/2015 | |
| WO | 2017021226 | 2/2017 | |

OTHER PUBLICATIONS

Office action dated May 7, 2020 issued by the Chinese Patent Office pertaining to Chinese Patent Application No. 201780013082.5.

* cited by examiner

REUSABLE MEDICATION DELIVERY DEVICE WITH REMAINING MEDICATION DETERMINATION CAPABILITY

BACKGROUND OF THE INVENTION

The present invention pertains to medication delivery devices, and, in particular, to medication delivery devices that are reusable with replacement cartridges.

Patients suffering from a number of different diseases frequently must inject themselves with medications. A variety of devices have been proposed to facilitate these injections. One known type of device is a reusable injection pen. Such an injection pen is typically equipped with a cartridge including a plunger and containing a multi-dose quantity of liquid medication. A drive f the pen is movable forward by a dose delivery mechanism to advance the plunger in the cartridge in such a manner to dispense the contained medication through a needle that penetrates a septum at a forward end of the cartridge. After such a pen has been utilized to deliver multiple doses and exhaust the supply of medication within the cartridge, a user can remove and dispose of the spent cartridge. After a user installs a replacement cartridge, the reusable injection pen then can be used again to deliver its medication contents in a conventional manner.

At least one known reusable injection pen utilizes an electronics assembly to determine a set and injected dose by monitoring relative motions of components used in setting a dose, and components used in advancing a drive screw to inject the set dose, respectively. While useful, one shortcoming of this pen is that it provides no mechanism to track the amount of medication remaining in a cartridge. While medication delivery device designs are known that can track drive screw position sufficiently accurately throughout its operational travel path, which would allow drive screw travel remaining and thereby medication remaining to be determined, such designs may add complexity to the device.

Thus, it would be desirable to provide a reusable delivery device that can overcome one or more of these and other shortcomings of the prior art.

BRIEF SUMMARY OF THE INVENTION

In one form thereof, the present invention provides a reusable medication delivery device for delivering medication from a cartridge having a barrel holding the medication between a movable plunger and an outlet. The reusable medication delivery device includes: a main housing; a cartridge housing adapted to removably receive the cartridge, the cartridge housing detachably mountable to the main housing; a drive member including a forward end for engaging the movable plunger, the drive member having a length extending in an axial direction within the main housing and including a sensible element along a portion of the length; a dose delivery mechanism for controlling advancement of the drive member forward within the main housing in the axial direction from a rearward position to a forward position, wherein advancement of the drive member forward in the axial direction, when the cartridge housing receives the cartridge and is mounted to the main housing, moves the movable plunger for delivering medication through the outlet; means for determining an amount of medicationdelivered by operation of the dose delivery mechanism; a first sensor for sensing either when the cartridge housing is mounted to the main housing or a presence of the cartridge within the cartridge housing when the cartridge housing is mounted to the main housing; at least one second sensor for sensing the sensible element as being located at a position within the main housing which is associated with the drive member being retracted to at least a first retraction position axially rearward of the forward position; and a controller in communication with the first sensor and the at least one second sensor and programmed to determine, based on inputs from the first sensor and the at least one second sensor, that a newly installed cartridge is to be considered full or not full of medication, the controller in communication with the determining means and programmed to calculate, based on an input from the determining means after a medication delivery, and if the cartridge was considered full when newly installed, a quantity of medication remaining in the installed cartridge after the medication delivery.

In another form thereof, the present invention provides a reusable medication delivery device for delivering medication from a cartridge assembly having a barrel holding the medication between a movable plunger and an outlet, the cartridge assembly including a first mounting element. The reusable medication delivery device includes: a main housing including a second mounting element cooperatively configured with the first mounting element for a detachable mounting of the cartridge assembly to the main housing; a drive member including a forward end for engaging the movable plunger, the drive member having a length extending in an axial direction within the main housing and including a sensible element along a portion of the length; a dose delivery mechanism for controlling advancement of the drive member forward within the main housing in the axial direction from a rearward position to a forward position, wherein advancement of the drive member forward in the axial direction, when the cartridge assembly is mounted to the main housing, moves the movable plunger for delivering medication through the outlet; means for determining an amount of medication delivered by operation of the dose delivery mechanism; a first sensor for sensing when the cartridge assembly is mounted to the main housing; at least one second sensor for sensing the sensible element as being located at a position within the main housing which is associated with the drive member being retracted to at least a first retraction position axially rearward of the forward position; and a controller in communication with the first sensor and the at least one second sensor and programmed to determine, based on inputs from the first sensor and the at least one second sensor, that a newly installed cartridge assembly is to be considered full or not full of medication, the controller in communication with the determining means and programmed to calculate, based on an input from the determining means after a medication delivery, and if the cartridge assembly was considered full when newly installed, a quantity of medication remaining in the installed cartridge assembly after the medication delivery.

One advantage of the present invention is that a reusable medication delivery device can be provided with a simple means to determine when a full cartridge is installed therein.

Another advantage of the present invention is that a reusable medication delivery device can be provided with the ability to track medication remaining in a ready fashion.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
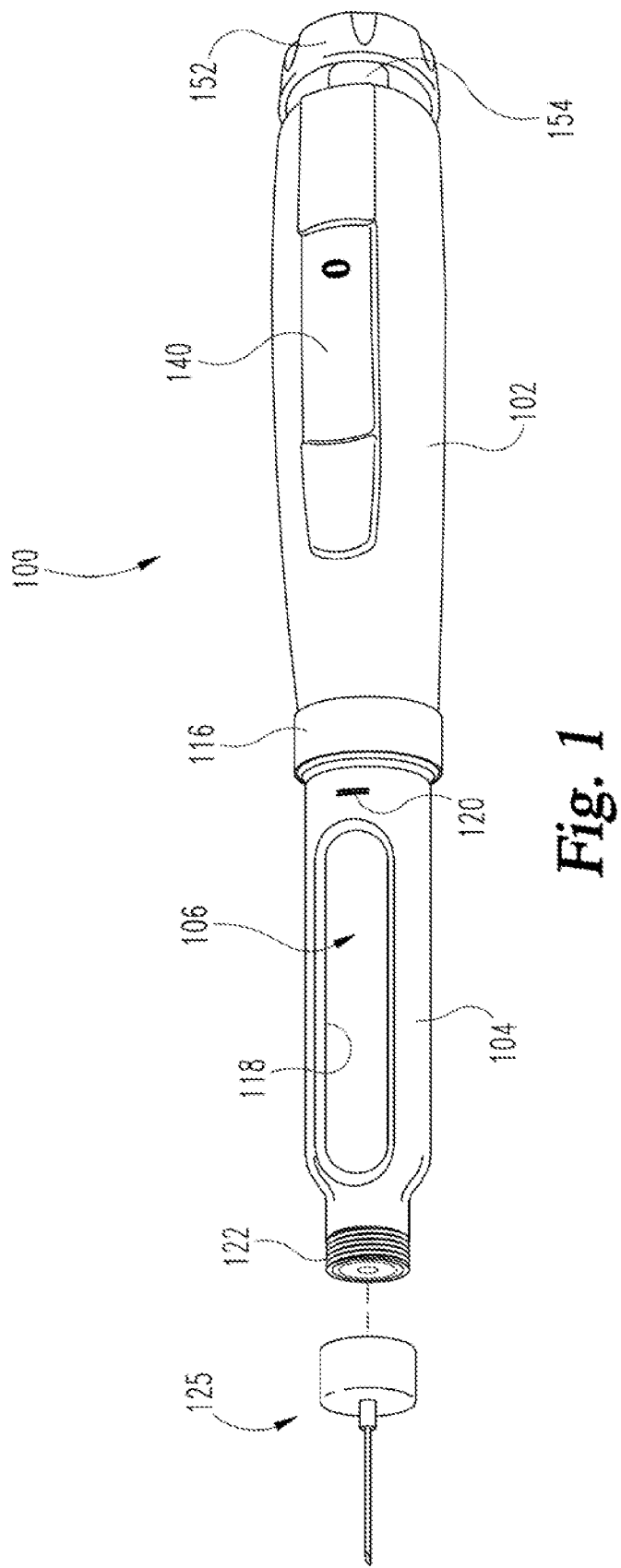
FIG. 1 is a perspective view of a reusable medication jection pen without a cap and prior to a mounting of a needle assembly.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION

Referring now to FIGS. 1-4, there is shown a reusable medication delivery device equipped with a sensing system that allows a determination of medication remaining after first recognizing as full a medication cartridge when newly installed in the device. The device is a reusable pen-shaped medication injection device, generally designated 100, which is manually handled by a user to selectively set a dose and then to inject that set dose. Injection devices of this type are well known, and the description of device 100 is merely illustrative as the sensing system can be adapted for use in variously constructed pen-shaped medication injection devices, as well as differently shaped injection devices and other medication delivery devices in general.

Medication injection device 100 includes a housing that supports the internal components of the device. The housing is shown as having a rear or main housing 102 and a forward or cartridge housing 104. Main housing 102 holds a mechanical drive mechanism of the device. Cartridge housing 104, also known as the cartridge retainer, holds a cartridge 106 filled with medication to be delivered by device operation. Cartridge retainer 104 is detachably mountable to main housing 102 via external threading 110 on a protruding collar portion 112 of main housing 102 which mates with internal threading 114 on a ring portion 116 at the proximal end of cartridge retainer 104. Suitable detachable mounting elements other than threadings 110 and 114 are known in the art and naturally may be employed, such as a bayonet fitting, or the use of an additional latching component.

Cartridge retainer 104 includes an internal hollow 105 suited to removably receive cartridge 106, thereby allowing a cartridge to be inserted therein, and then removed therefrom when depleted and replaced with a fresh cartridge of similar design. Openings 118 in cartridge retainer 104 allow visibility of the cartridge contents. A detent feature 120 provided on the exterior of cartridge retainer 104 allows for a not shown protective cap to be detachably mounted over the cartridge retainer 104 when a needle assembly 125 is not attached to the cartridge retainer 104. Although cartridge retainer 104 is described herein as being a reusable component, the cartridge retainer 104 could be integrated with, and therefore be disposable with, the cartridge 106.

Medication cartridge 106 is of conventional design, including a barrel 130 having an interior reservoir filled with medication which is sealed at one end by a slidable plunger or piston 132 and sealed at the other end by a septum 134 held by a crimp ring 136.

A needle assembly 125 detachably mountable to an externally threaded proximal end 122 of cartridge retainer 104 pierces the septum 134 when so mounted. The pierced septum through which the needle extends serves as an outlet during dispensing for the medication within the reservoir of barrel 130, which medication is delivered through the needle assembly 125 by operation of device 100. The cartridge 106 can hold multiple doses of medication, or even a single dose, depending on the purpose of device 100.

Figure 2:
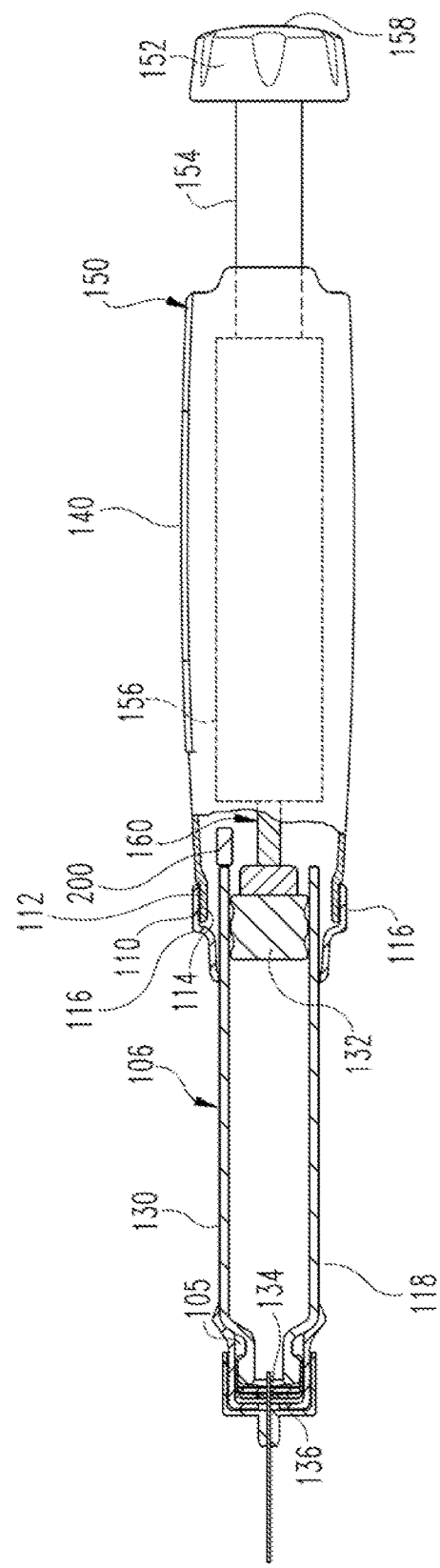
FIG. 2 is a side view in partial cross-section of the injection pen of FIG. 1 with a needle assembly attached and after a dose for delivery has been set.

Medication injection device 100 is shown in FIG. 1 in its "zero position" at which the device has not been set for delivery of any dose. This zero position setting is indicated by the number "0" visible on the dose display 140 in FIG. 1. In FIG. 2, device 100 is arranged after being manipulated to set a dose of thirty units for delivery, and the number "30" would be visible on the display 140.

Medication injection device 100 is typical of many such reusable devices in including a manually-powered dose delivery chanism, generally designated 150, that controls forward advancement of a drive member, generally designated 160. Drive member 160 advances within the cartridge barrel 130 to directly engage and advance plunger 132 As shown in FIG. 2, dose delivery mechanism 150 includes a dose knob 152 connected via a tube 154 to a mechanical drive assembly abstractly indicated at 156 that is housed within main housing 102. When knob 152 is turned by a user to set a dose for injection, dose knob 152 and tube 154 screw out together from main housing 102. When a user applies a plunging force on the proximal end 158 of dose knob 152, the resulting simply translational motion of dose knob 152 and tube 154 forward into main housing 102 is converted by drive assembly 156 into a smaller motion of drive member 160 forward from main housing 102 into the interior of cartridge barrel 130.

Drive member 160 is formed in two pieces including a forward end 163 that directly engages the cartridge plunger 132, and a shaft 165 that axially extends rearward from forward end 163 into main housing 102. The shaft 165 is threaded at 167 and is engaged with drive assembly 156 to be screwed out from main housing 102 as it is driven forward. Forward end 163 is provided in the form of an enlarged foot that is mounted on shaft 165 to allow relative rotation, allowing foot 163 to engage plunger 132 without relative rotation therebetween as shaft 165 screws out. While this foot and shaft two-piece construction of drive member 160 is preferred when shaft 165 screws out from the housing during advancement, such a construction is not required in devices, particularly if the drive member simply translates within the housing, in which case a single piece drive member construction may be more acceptable.

Device 100 uses an electronic dose display 140 rather than a helically marked dial display as used in many other reusable injection devices. Display 140 is circuited to and controlled by an electronic controller or computing assembly 170 mounted within main housing 102. Controller 170 is programmed and has memory sufficient to achieve the electronic features of device 100. The set dose displayed in display 140 is determined by the interaction of dose delivery mechanism 150 with a sensor mechanism or system, abstractly shown at 175, which is circuited with and controlled by controller 170. Such a sensor mechanism 175 can be, for example, an electrical, magnetic, optical, audible, ultrasonic or other sensing technology as is known in the art. Provided sensor mechanism 175 is equipped with a feature as is known in the art allowing the controller 170 to recognize when a set dose is in fact delivered, such sensor mechanism 175 can serve to determine the amount of medication delivered by dose delivery mechanism 150 when operated to deliver the set dose. Alternatively, other mechanisms to determine the amount of medication delivered by operation of dose delivery mechanism 150 may be used in device 100. Such an alternate mechanism includes a system that does not sense the amount of a set dose but merely senses, such as using electrical, magnetic, optical, audible, inductive or other sensing means as is known in the art, a delivered dose, including but not limited to a sensor mechanism that determines positions of, for example, a drive element before and after an injection to allow a dose delivery amount to be calculated by the controller based on the distance the drive element is sensed to have moved.

The foregoing description of device 100 is intended to be illustrative and not limiting as the sensing system that allows determination. of medication remaining in a cartridge as described further below may be used in other differently configured devices. Device 100 is similar in many respects to a device described in International Publication Number WO 02/092153, which publication is incorporated herein by reference in its entirety.

The system for determining remaining medication uses both a sensor for sensing drive member 160, and a sensor for sensing the cartridge 106 and/or cartridge retainer 104.

The drive member sensing sensor 190 is mounted within main housing 102 and circuited with and controlled by controller 170. Sensor 190, which may be composed of a single sensing element or an array of multiple sensing elements, serves to sense the sensible element, generally indicated at 194, of drive member 160.

Sensor 190 is fixed within the length of main housing 102 in order to sense sensible element 194 to allow a determination of whether drive member 160 is pushed back from a fully advanced or forward position a distance needed to accommodate a new full cartridge. One possible positioning of sensor 190 within housing 102 is at a sensing point, or a point slightly forward of such point, where it is triggered by the sensible element 194 just as the forward end 163 of drive member 160 reaches an axial position at which it could be expected to abut or initially engage the proximal face of a plunger 132 in a full cartridge 106 that is within the fully assembled device 100. The axial position of the drive member 160 at such arrangement is known as the cartridge full retracted position, though it will be appreciated that variability due to tolerances of the device and the cartridges means the drive meq ber 160 might be slightly differently so positioned within the housing from cartridge to cartridge. For example, some cartridges are nominally 300 unit cartridges. The sensor 190 may be positioned within main housing 102 at a position where it is triggered by sensing element 194 when the drive member 160 is retracted a distance corresponding to 295-300 units of delivery from the fully advanced forward position, where the 300 units of delivery position may be considered the cartridge full retracted position.

The positioning of sensor 190 may be forward or rearward of these points, but preferably is not so far rearward within the main housing 102 that is might fail to recognize a drive member that is merely retracted sufficiently far for the smallest full cartridge within tolerances with which the device may be used. For example, in at least some reusable injection devices, the drive member can be manually pushed back into the housing during device resetting a distance that is farther than required to accommodate a full cartridge within tolerances then loaded into the device for use. Having the sensor 190 be triggered only when the drive member 160 is pushed all the way back to its physical stop in such a device would lead to the device not recognizing some or possibly all cartridges that should be considered full.

Sensor 190 may be positioned more forward of the sensing point than as described above if the possibility of false positive recognitions are acceptable, particularly if a checking feature as described further below is implemented. For example, and again for a nominally 300 unit cartridge, the sensor 190 may be positioned within main housing 102 at a position where it is triggered by sensing element 194 when the drive member 160 is retracted a distance corresponding to, for example, any of 250, 260, 270, 280 or 290 units of delivery from the fully advanced forward position, especially if positioning the sensor at, for example, 300 units would require the device to be unacceptably longer.

Alternatively considered, and considering the total possible travel distance a drive member can move relative to the main housing to be equal to the distance between where the drive member is located when fully advanced forward and where the drive member is located when filly manually pushed rearward during reset, sensor 190 can be positioned up to, for example, one-half, or a third, or a fourth, or a fifth of such total possible travel distance forward of such sensing point.

One suitable type of sensor for sensor 190 is a magnet sensor that generates signal that goes form a low amplitude to a high amplitude as the sensible element 194 passes by, or passes through a point at which transverse to the axial direction it is aligned with, sensor 190 when moving in the rearward or retraction direction. Such change in amplitude can be considered a switch triggering. The change from low amplitude to high amplitude is not instantaneous but rather has a transition slope during sensible element travel, with stronger magnets for sensible element 194 producing steeper transition slopes.

As sensible element 194 on driver member 160 continues to be further retracted from where the signal transitions, the signal generated by sensor 190 tapers slowly in amplitude but continues to have a relatively high value. As sensible element 194 on driver member 160 moves forward from where the signal transitions, the signal generated by sensor 190, over the range of distances possible in device 100, rises slightly in amplitude but continues to have a relatively low value. For these high and low signals, the signal resolution is not sufficiently precise to allow a device controller to determine an exact axial position of the drive member 160 within the housing suitable to allow dose amounts, or delivery volume remaining, to be calculated. The relatively high amplitude of the output of sensor 190 when drive member 160 is retracted beyond a point of transverse alignment with sensor 190 allows the controller to recognize the drive member as being retracted within a range of positions rearward of the aligned position. This allows a sensing of an over retraction of drive member 160, such as if a user, while device 100 was disassembled and in preparation of loading a replacement cartridge 106, manually pushes the drive member 160 rearward into the main housing 102 farther than is needed to prepare for a new full cartridge. The controller can be programmed to consider a signal amplitude found within the signal transition period to be the point at which it considers alignment to have occurred, and the high amplitude and low amplitude outputs otherwise more typically produced by the sensor 190 would be readily recognized as occurring on opposite sides of such alignment point.

Figure 3:
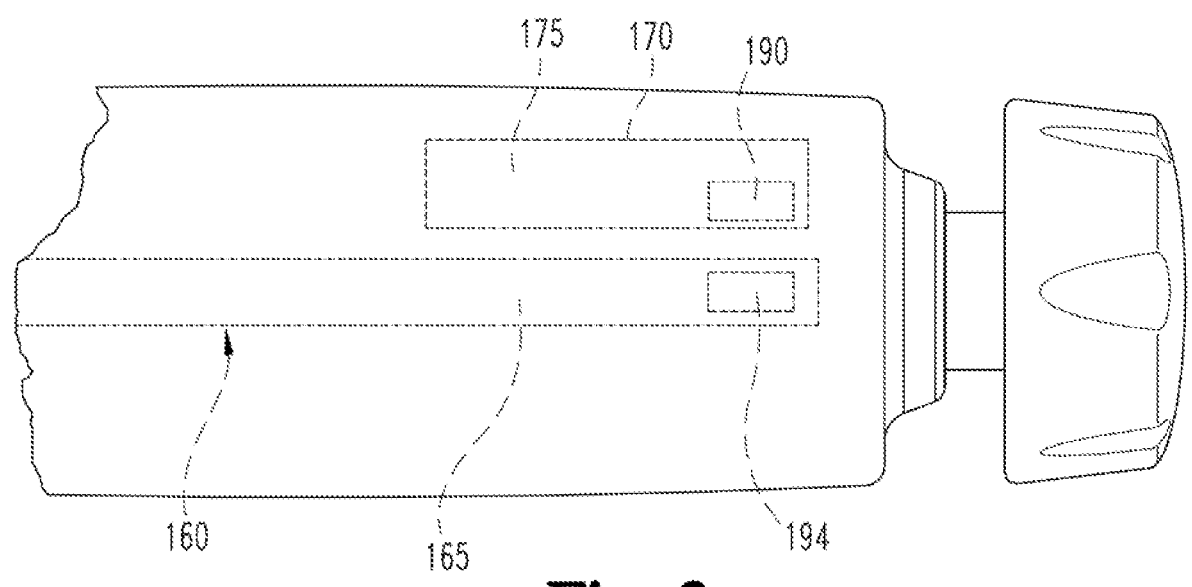
FIG. 3 is a partial bottom view of the injection pen of FIG. 1 illustrating aspects of a system for determining remaining medication.

With reference to FIG. 3, sensible element 194 is abstractly shown as a discrete feature provided on drive member shaft 165 near the rearward end of that shaft. A suitable sensible element 194 may be a magnet with its opposite magnetic poles being on opposite axial ends of the sensible element. Alternatively, sensible element 194 could be another form of specialized element coordinated with a complementary sensor 190. For example, sensible element 194 could be a reflective coating or a character that is readily sensed by an optical sensor 190. Still further, the sensible element 194 could be the rear end face of shaft 165 that contacts an electrical switch serving as sensor 190, or that otherwise may be sensed as being present or absent, such as by an optical sensor 190. Other sensing technologies that are known, such as inductive or ultrasonic, alternatively may be used.

Although sensible element 194 is shown fixed in the rear end of shaft 165, such a positioning is a not required to practice the present invention but is preferred. In the shown embodiment, in which controller 170 is located within the rearward portion of housing 102, such a positioning of sensible element 194 is useful as sensor 190 can be positioned within the rearward portion of housing 102 and the length of the electrical connection between sensor 190 and controller 170, be it via spanning wiring or otherwise such as a conductive track on a printed circuit board, is short. Sensible element 194 could be otherwise provided along the length of shaft 165, such as in the middle or near the forward end of the shaft 165, if a corresponding positional change of sensor 190 within housing 102 were made.

The sensor for sensing the cartridge 106 is shown at 200 in FIG. 2. Sensor 200 is mounted within housing 102 and circuited with controller 170. Sensor 200 is constructed to sense the presence or absence of a cartridge 106 when housing portions 102 and 104 are operationally assembled for device use. Different types of sensors may be used for sensor 200, with appropriate adaptation of cartridge 106 if needed, such as an electrical switch or a magnetic or optical sensor. Although shown as directly sensing the cartridge, sensor 200 can indirectly sense the cartridge presence, such as by sensing the position of a device component, such as a drive member-engaging nut, which is moved by contact with a cartridge installed when the housing portions 102 and 104 are assembled for use.

Rather than sensing the presence or absence of cartridge 106, sensor 200 could be positioned to sense the presence of absence of cartridge retainer 104 operationally assembled to housing 102. As with sensing of the cartridge described above, such retainer sensing could be done either directly or indirectly. In a retainer sensing scenario, the user would be required to ensure that a cartridge was loaded within that retainer 104 in order for the remaining dose information. that can be provided by device 100 as described below to be of any value. In a scenario where the cartridge and retainer were integrated by the manufacturer to be handled as a single cartridge assembly that is disposable as a unit after the cartridge contents are exhausted, the sensor 200 could be adapted to sense the presence of absence of the cartridge assembly mounted to housing 102, again either directly or indirectly.

Sensors 200 and 190 are utilized by controller 170 to determine when a new, full cartridge has been loaded into device 100, so that remaining medication in that cartridge can be tracked thereafter. Controller 170 continuously monitors the signal from sensor 200. When the signal from sensor 200 changes from one associated with no cartridge sensed as present to e associated with a cartridge 106 being sensed as present, controller 170 understands or recognizes that device 100 has been assembled with a cartridge 106 loaded within cartridge retainer 104.

When a cartridge 106 is so recognized as present, controller 170 considers the signal from sensor 190. if the signal that sensor 190 sends to controller 170 is recognized by controller 170 as drive member 160 of device 100 being in a position at which the sensible element 194 is aligned with, or rearward of the sensor 190, the controller 170 associates this combination of signals from sensors 200 and 190 as a newly loaded cartridge 106 being a full cartridge. Such a full cartridge status can be shown on display 140, or a display on a device with which controller 170 is linked.

Controller 170 can then keep track of medication remaining in the cartridge 106 throughout the use of device 100 until controller 170 recgnizes, due to a change in signal from sensor 200, that cartridge 106 is no longer present. Such tracking is performed by controller 170 subtracting, from the original quantity the controller is programmed to expect in a full cartridge, amounts that the device 100 is sensed as subsequently dispensing during one or more operations, such as by tracking the information provided by sensor system 175 during injecting operations. The amount calculated by controller 170 to be remaining in the cartridge 106 at any given time can be displayed in display 140, or a display of a smart device such as a phone if the device 100 is linked to it. The user may be notified on such a display of the remaining volume at different times, such as after each dispensing or whenever the pen is turned or when the user manipulates the pen or smart device to query the controller 170 as to the medication remaining.

If sensor 190 is positioned forward of where the sensible element is located when the drive member 160 is in a cartridge full retraction position, it is possible that a newly installed cartridge that the controller 170 believes to be full is not so. The device controller 170 can be programmed to perform checks during later use that identify such fact and then inform the user that remaining medication tracking is not possible for the loaded cartridge. For example, if the sensor 190 were positioned a distance corresponding to 250 units of delivery from the fully advanced forward position of the drive member, controller 170 would expect sensor 190 to identify, via a change in signal from high to low, sensible element 194 being aligned with the sensor 190 after approximately fifty units have delivered during normal use from the cartridge initially determined to be full. Controller 170 can be programmed to recognize that during subsequent device use, when input from sensor 190 is recognized by controller 170 as sensible element 194 having reached sensor 190 sooner than would have been expected had the installed cartridge been full, that a not full cartridge had been installed previously. For the above example, if a cartridge filled with 270 units had been newly installed, which cartridge would have been thought by controller 170 to have been full of 300 units, the fact that the sensor 190 will change its output after twenty units have been delivered, as opposed to fifty units as expected by the controller, will cause the controller 170 to recognize the prior error in believing the cartridge was full. The controller 170 will understand that the calculated quantity of medication remaining in the installed cartridge after medication delivery is not reliable in such a circumstance, and can send an appropriate message to the user in display 140, or other linked display, such as "medication remaining tracking no longer available for this cartridge".

It will be appreciated that controller 70 can account for different concentrations of medication in cartridge 106, such as by working with a sensor of info about the concentration from the cartridge, or by a user inputting such info into device 100 either directly by device manipulation or via an electronic downloading of such information, such that the medication amount remaining, as well as dose set and injected, can be tracked as units and not volume. The controller may also track the actual time, or relative time of cartridge changes, which can then be communicated wirelessly to an external device, such as a smartphone having an application that accepts and uses such data. The controller also may monitor device states that indicate errors or malfunctions that can be alerted on the display or wirelessly sent to a remote device, such as a smartphone.

Figure 4:
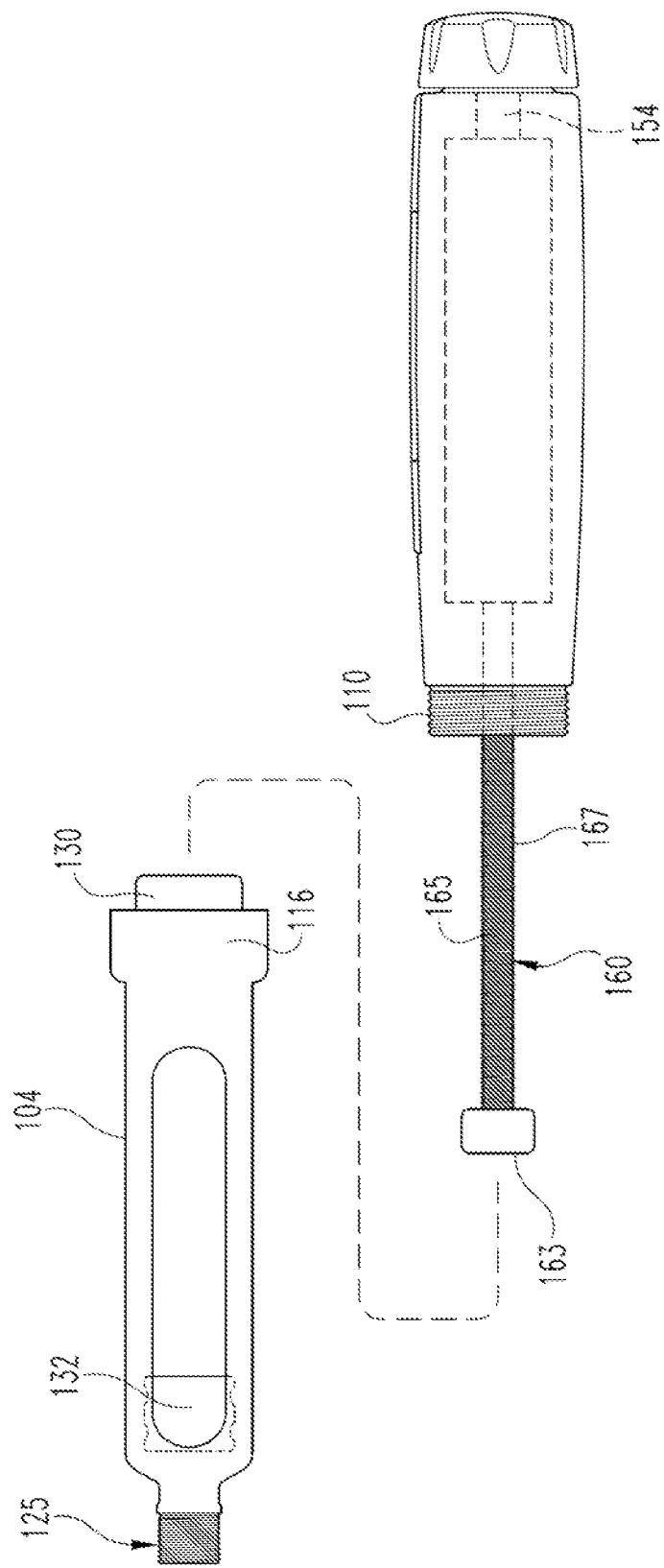
FIG. 4 is a side view of the injection pen of FIG. 1 in a state of disassembly after its held cartridge has been exhausted of deliverable medication.

When the cartridge contents are exhausted by reason of the drive member 160 having been advanced by medication dispensing operations of device 100, the user can disassemble retainer 104 from main housing 102 by unscrewing them apart. Such a disassembled state is shown in FIG. 4. When so disassembled, the sial sent by sensor 200 to controller 170 is recognized as cartridge 106 being no longer present in device 100. Display 140 can be controlled to indicate that no cartridge is present in the device 100.

A user then can prepare the device 100 for future operation in the following manner After removing the spent cartridge 106 from retainer 104 and inserting a. replacement cartridge 106 in the retainer 104, the user can arrange the retainer 104 and main housing 102 such that the drive member forward end 163 is insertably aligned with the cartridge barrel 130, and then the retainer 104 and main housing 102 can be moved together axially and operationally secured, causing the drive member 160 to be driven rearward by the contact of forward end 163 with the rear face of cartridge plunger 132 . After such an assembling of retainer 104 with main housing 102, controller 170 will again recognize the presence of cartridge 106, due to the input from sensor 200. Further, it will be appreciated that if the cartridge 106 in retainer 104 is full, the drive member 160 will have been shifted rearward to a point that sensible element 194 reached or passed sensor 190, allowing the controller 170 to recognize that a full cartridge is present and that medication remaining can then be tracked as described above. If, however, sensor 190 does not sense that sensible element 194 has reached or passed it, controller 170 will recognize that a partially full, or previously used, cartridge 106 was installed and provide an appropriate message to the user in display 140, or other linked display, such as "partially filled cartridge installed" or "no medication remaining tracking available for this cartridge".

It will be understood that some users, when assembling device 100 with a new cartridge 106 in retainer 104, may manually push drive member 160 back into main housing 102 with her finger, fbr example, prior to attaching retainer 104 to main housing 102. In such a situation, if the drive member 160 is pushed back beyond the cartridge full retraction position, the preferred ability of sensor 190 to recognize sensible element 194 and output a high signal allows controller 170 to assume a full cartridge has been installed. The controller can still track remaining dose for such a configuration, starting with the programmed number of units in a full cartridge. Since the maximum distance beyond the cartridge full retraction position that drive member 160 can be pushed back manually in at least some devices is relatively small, any wastage of medication associated with controller 170 identifying the cartridge contents as being exhausted after an expected number of units have been expelled, despite the fact that the drive member 160 may still be able to move forward within the cartridge 106 in such devices, is an acceptable amount.

While this invention has been shown and described as having preferred designs, the present invention may be modified within the spirit and scope of this disclosure. For example, each device could be calibrated when manufactured to determine the output value of sensor 190, within the transitioning between relatively low and high signals, that best corresponds to the transverse alignment of the sensible element 194 with sensor 190, which output value when stored into the controller to use as a threshold value would provide even greater certainty in a device as to whether a cartridge was full when installed. This application is therefore intended to cover any variations, uses or adaptations of the invention using its general principles. Further, this application is intended to cover such departures from the present disclosure as come within known or customary practice in the art to which this invention pertains.

We claim:

1. A reusable medication delivery device for delivering medication from a cartridge having a barrel holding the medication between a movable plunger and an outlet, the reusable medication delivery device comprising:
   a main housing;
   a cartridge housing adapted to removably receive the cartridge, said cartridge housing detachably mountable to said main housing;
   a drive member including a forward end for engaging the movable plunger, said drive member having a length extending in an axial direction within the main housing and including a sensible element along a portion of said length;
   a dose delivery mechanism for controlling advancement of said drive member forward within the main housing in the axial direction from a rearward position to a forward position, wherein advancement of said drive member forward in the axial direction, when the cartridge housing receives the cartridge and is mounted to the main housing, moves the movable plunger for delivering medication through the outlet;
   means for determining an amount of medication delivered by operation of said dose delivery mechanism;
   a first sensor for sensing either when said cartridge housing is mounted to said main housing or a presence of the cartridge within said cartridge housing when said cartridge housing is mounted to said main housing;
   at least one second sensor for sensing said sensible element being located at a position within said main housing which is associated with said drive member being retracted to at least a first retraction position axially rearward of said forward position; and
   a controller in communication with said first sensor and said at least one second sensor and programmed to determine, based on inputs from said first sensor and said at least one second sensor, that a newly installed cartridge is to be considered full or not full of medication, said controller in communication with said determining means and programmed to calculate, based on an input from said determining means after a medication delivery, and if the cartridge was considered full when newly installed, a quantity of medication remaining in the installed cartridge after the medication delivery.

2. The reusable medication delivery device of claim 1 wherein said at least one second sensor comprises a magnetic sensor.

3. The reusable medication delivery device of claim 2 wherein said sensible element comprises a magnet disposed at a rearward end of said length of said drive member.

4. The reusable medication delivery device of claim 1 wherein said first retraction position is associated with an initial engagement of a movable plunger of a full cartridge.

5. The reusable medication delivery device of claim 1 wherein said first retraction position is a first amount axially forward of a position associated with an initial engagement of a movable plunger of a full cartridge, said first amount equal to or less than one-half of a total possible travel distance of said drive member relative to said main housing.

6. The reusable medication delivery device of claim 5 wherein said first amount is equal to or less than a third of a total possible travel distance of said drive member relative to said main housing.

7. The reusable medication delivery device of claim 5 wherein said first amount is equal to or less than a fourth of a total possible travel distance of said drive member relative to said main housing.

8. The reusable medication delivery device of claim 5 wherein said first amount is equal to or less than a fifth of a total possible travel distance of said drive member relative to said main housing.

9. The reusable medication delivery device of claim 1 wherein said first retraction position is axially forward of a position associated with an initial engagement of a movable plunger of a full cartridge, and wherein if the controller determines the cartridge to be full when newly installed, said controller recognizes during subsequent device use, when input from said at least one second sensor is recognized by said controller as said drive member sensible element having reached said at least one second sensor sooner than would have been expected had the installed cartridge been full, that a not full cartridge had been installed previously and that further calculated quantities of medication remaining in the installed cartridge after medication delivery are not reliable.

10. The reusable medication delivery device of claim 1 wherein any input ftom said at least one second sensor when said drive member is disposed forward of said first retraction position is different from input from said at least one second sensor when said drive member is disposed rearward of said first retraction position, said any input from said at least one second sensor when said drive member is disposed forward of said first retraction position being insufficiently precise so as to preclude said controller from determining an exact axial position of said drive member.

11. The reusable medication delivery device of claim 10 wherein said input from said at least one second sensor when said drive member is disposed rearward of said first retraction position is insufficiently precise so as to preclude said controller from determining an exact axial position of said drive member.

12. The reusable medication delivery device of claim 10 wherein an amplitude of any input from said at least one second sensor when said drive member is disposed forward of said first retraction position is below a threshold level, and an amplitude of said input from said at least one second sensor when said drive member is disposed rearward of said first retraction position is above the threshold level.

13. The reusable medication delivery device of claim 1 wherein said determining means operates without input from said at least one second sensor.

14. The reusable medication delivery device of claim 13 wherein said determining means operates without sensing said drive member.

15. The reusable medication delivery device of claim 1 further comprising a display upon which is displayed, if the cartridge is considered full when newly installed, the quantity of medication remaining in the installed cartridge after medication delivery.

16. The reusable medication delivery device of claim 1 further comprising a display upon which a notification that medication remaining tracking is not available is displayed when said controller, based on inputs from said first sensor and said at least one second sensor, determines that the newly installed cartridge is to be considered not full of medication.

17. The reusable medication delivery device of claim 1 wherein said first sensor senses the presence of the cartridge within said cartridge housing when said cartridge housing is mounted to said main housing.

18. A reusable medication delivery device for delivering medication from a cartridge assembly having a barrel holding the nedication between a movable plunger and an outlet, the cartridge assembly including a first mounting element, the reusable medication delivery device comprising:
    a main housing including a second mounting element cooperatively configured with the first mounting element for a detachable of the cartridge assembly to said main housing;
    a drive member including a forward end for engaging the movable plunger, said drive member having a length extending in an axial direction within the main housing and including a sensible element along a portion of said length;
    a dose delivery mechanism for controlling advancement of said drive member forward within the main housing in the axial direction from a rearward position to a forward position, wherein advancement of said drive member forward in the axial direction, when the cartridge assembly is mounted to the main housing, moves the movable plunger for delivering medication through the outlet;
    means for determining an amount of medication delivered by operation of said dose delivery mechanism;
    a first sensor for sensing when said cartridge assembly is mounted to said main housing;
    at least one second sensor for sensing said sensible element as being located at a position within said main housing which is associated with said drive member being retracted to at least a first retraction position axially rearward of said forward position; and
    a controller in co anon with said first sensor and said at least one second sensor and programmed to determine, based on inputs from said first sensor and said at least one second sensor, that a newly installed cartridge assembly is to be considered full or not full of medication, said controller in communication with said determining means and programmed to calculate, based on an input from said determining means after a medication delivery, and if the cartridge assembly was considered full when newly installed, a quantity of medication remaining in the installed cartridge assembly after the medication delivery.

19. The reusable medication delivery device of claim 18 wherein said first retraction position is associated with an initial engagement of a movable plunger of a full cartridge assembly.

20. The reusable medication delivery device of claim 18 wherein said first retraction position is a first amount axially forward of a position associated with an initial engagement of a movable plunger of a full cartridge assembly, wherein said first amount is equal to or less than a fourth of a total possible travel distance of said drive member relative to said main housing.

21. The reusable medication delivery device of claim 18 wherein said first retraction position is axially forward of a position associated with an initial engagement of a movable plunger of a full cartridge assembly, and wherein if the controller determines the cartridge assembly to be full when newly installed, said controller recognizes during subsequent device use, when input from said at least one second sensor is recognized by said controller as said drive member sensible element having reached said at least one second sensor sooner than would have been expected had the installed cartridge assembly been full, that a not full cartridge assembly had been installed previously and that further calculated quantities of medication remaining in the installed cartridge assembly after medication delivery are not reliable.

22. The reusable medication delivery device of claim 18 further comprising a display upon which is displayed, if the cartridge assembly is considered full when newly installed, the quantity of medication remaining in the installed cartridge assembly after medication delivery.

23. The reusable medication delivery device of claim 18 further comprising a display upon which a notification that medication remaining tracking is not available is displayed when said controller, based on inputs from said first sensor and said at least one second sensor, determines that the newly installed cartridge assembly is to be considered not full of medication.

* * * * *